United States Patent [19]

Doyle

[11] Patent Number: 4,835,389
[45] Date of Patent: May 30, 1989

[54] INTERNAL REFLECTION SPECTROSCOPY FOR DEEP CONTAINER IMMERSION

[75] Inventor: Walter M. Doyle, Laguna Beach, Calif.

[73] Assignee: Laser Precision Corporation, Irvine, Calif.

[21] Appl. No.: 158,214

[22] Filed: Feb. 19, 1988

[51] Int. Cl.⁴ .................... G01N 21/35; G01N 21/84
[52] U.S. Cl. .................................... 250/343; 356/436
[58] Field of Search .................. 356/136, 436, 346; 250/343, 573, 574

[56] References Cited
U.S. PATENT DOCUMENTS
3,751,672  8/1973  Michel et al. ................. 250/574

Primary Examiner—Vincent P. McGraw
Attorney, Agent, or Firm—Thomas J. Plante

[57] ABSTRACT

A spectroscopy system is disclosed which obtains analytical information from an internal reflectance element (IRE) deeply immersed in a container. The system is designed to provide adequate radiation throughput under difficult conditions. A plurality of embodiments deal with the optical element(s) at the bottom of the tube and the optical element(s) above the tube which direct post-interference radiation downward in the tube and receive post IRE upward radiation for re-direction to the detector.

14 Claims, 6 Drawing Sheets

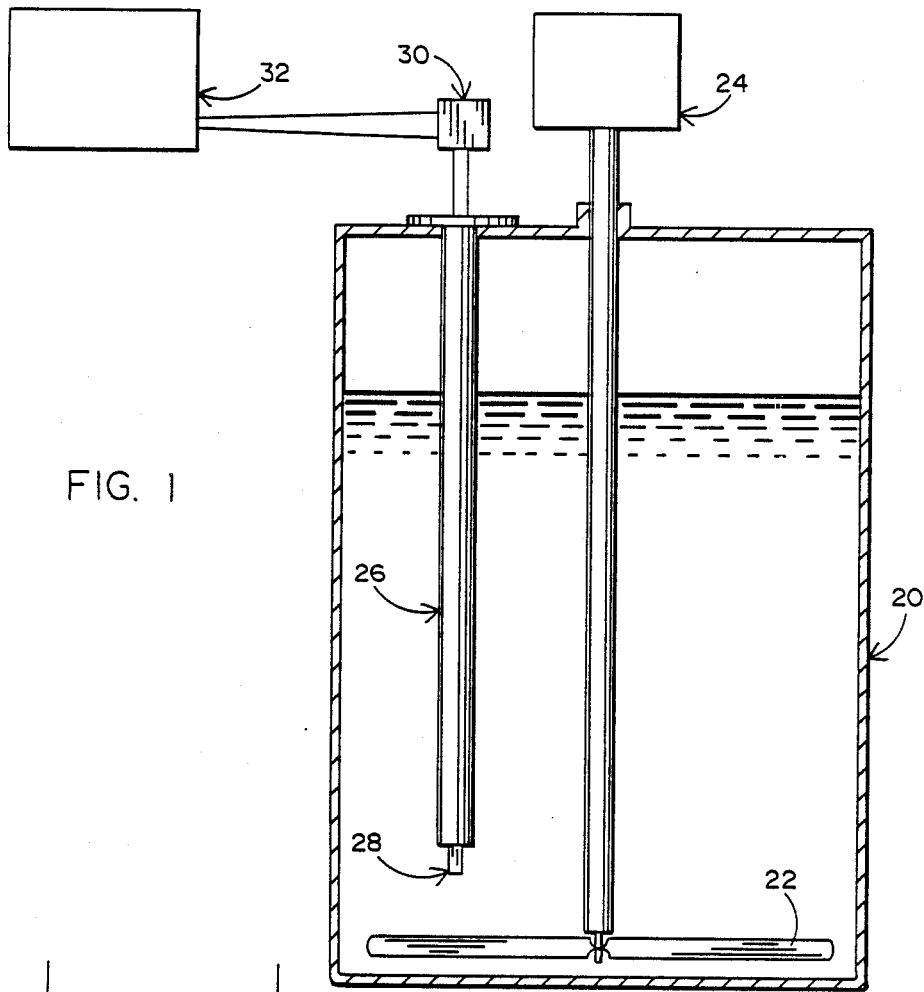
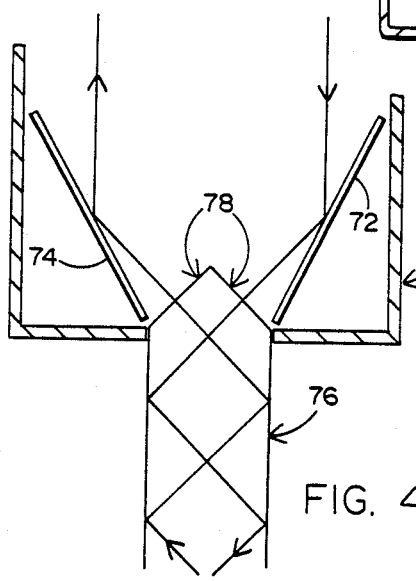
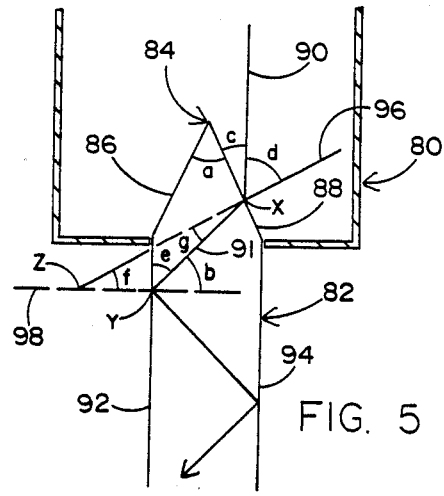
FIG. 1
FIG. 4
FIG. 5

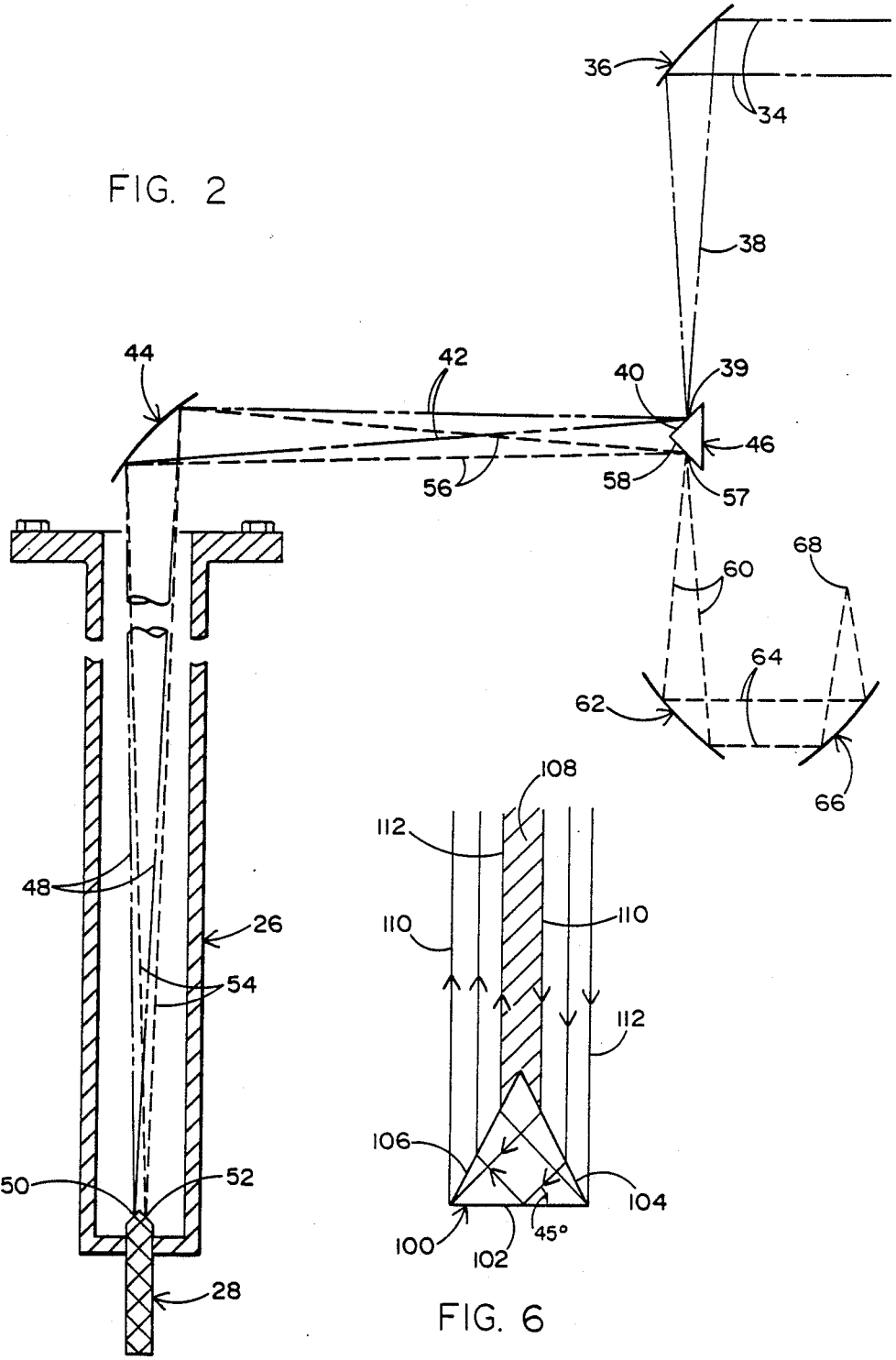

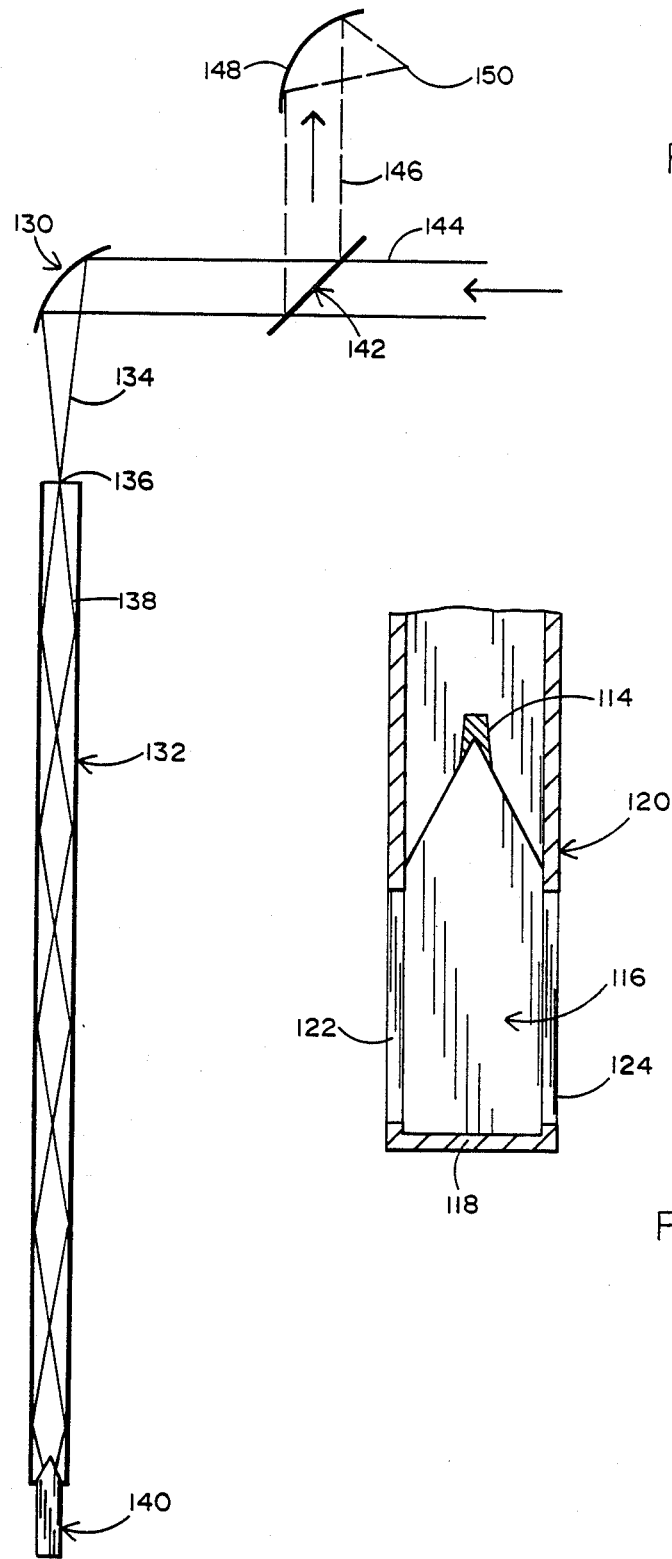

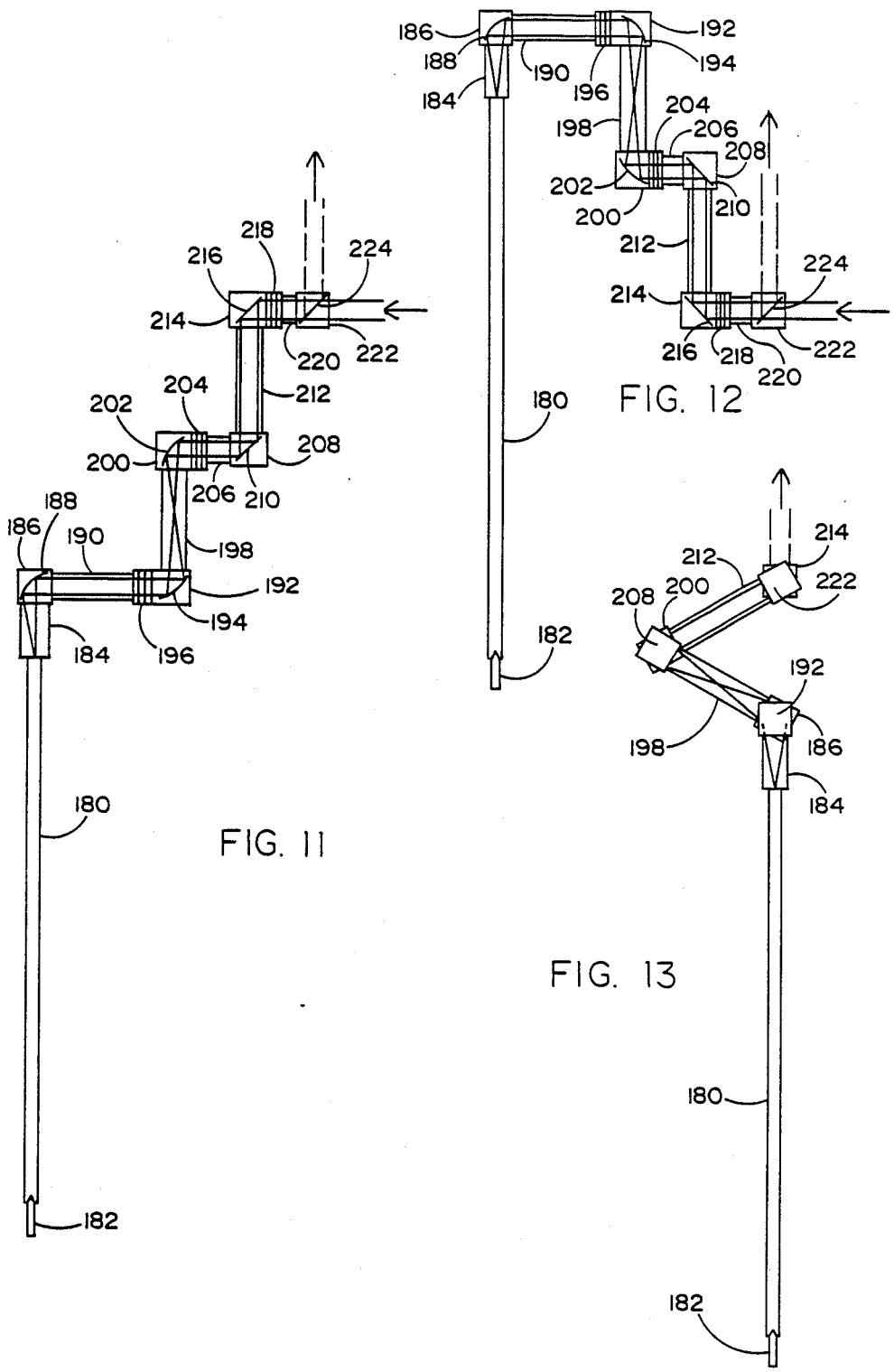

INTERNAL REFLECTION SPECTROSCOPY FOR DEEP CONTAINER IMMERSION

BACKGROUND OF THE INVENTION

This invention relates to internal reflection spectroscopy; and its primary purpose is to provide an apparatus which permits relatively deep immersion of an internal reflectance accessory into a container whose contents are to be spectroscopically analyzed.

An accessory referred to as a "prism liquid cell" is marketed by Harrick Scientific Corporation. This accessory is used to replace "amalgamated sealed cells", which were previously used to hold sample material, through which radiation was passed to provide transmission spectroscopy.

In internal reflection spectroscopy by an accessory extending into the sample material, an internally reflecting element (IRE) is surrounded by the sample; and the analytical radiation is essentially confined inside the IRE. Infrared light enters and leaves the IRE from one end, which in the Harrick accessory has the shape of a 90° rooftop. The Harrick accessory is a rectangular cross-section crystal (typically composed of zinc selenide) having its outer (non-immersed) end cut at an angle of 45° to each of its long sides.

Infrared light from a source enters the first inclined side of the IRE rooftop, generally on a perpendicular path. The infrared light is reflected first from one wall of the IRE, then from the opposite wall of the IRE, and so on, until it reaches, and is reflected by, the end of the IRE. It is then returned, along a path parallel to the incoming radiation, by reflection back and forth across the IRE until it exits the IRE from the second inclined side of the rooftop. And it is then directed to an infrared detector.

If the IRE (also referred to as a prism or crystal) is surrounded by air, the internal radiation from the source will be totally reflected. However, if the IRE is in contact with an infrared absorbing material, such as a liquid chemical, the radiation will be selectively absorbed at various wavelengths, resulting in an infrared spectrum. The amount of radiation absorbed is influenced by the angle of incidence of the radiation on the sides of the IRE.

IREs are often referred to as attenuated total reflectance (ATR) crystals, because the internal reflectance permits a limited amount of light absorption by the sample surrounding the crystal. The angle of incidence of the internal light on the crystal walls must be at or above the critical angle. If the angle of incidence is too small, excessive radiation will leave the crystal and be absorbed by the sample. If the angle of incidence is too large, excessive radiation will be internally reflected, and insufficient radiation will be absorbed by the sample to provide adequate analytical information. In other words, sample absorption of radiation is necessary, but sufficient radiation must return and exit from the crystal on its way to the detector.

There is a major need for a sample analyzing spectroscopic accessory which can extend deeply inside a container. Such an accessory would be invaluable in providing information during processing of the contents of the container. It would also permit ready evaluation of the condition of previously stored materials.

In situations where higher frequency radiation is useful (e.g., in the visible range), fiber optic light transmission may be used to get the radiation into and out of the deeply immersed IRE. However, the use of fiber optic transmission for infrared radiation is prohibitively expensive.

SUMMARY OF THE INVENTION

The present invention provides, for the first time, an effective apparatus for extending infrared spectroscopy to a substantial depth inside a container, thus permitting in situ spectroscopic analysis in situations where such analysis has not heretofore been practical.

In accomplishing this result, this invention combines (a) an elongated tube extending downwardly from the top of a container with (b) an IRE (or ATR crystal) mounted on the lower end of the tube. Infrared radiation is directed into the top of the tube, passes down to the IRE, is internally reflected in the IRE, and returns on a parallel path upwardly through the tube.

The optical control of the radiation is crucial at two locations: (a) at the location where it enters into and exits from the tube, and (b) at the location where it enters into and exits from the IRE. At the top of the tube, it is desirable to employ the maximum possible aperture area, while providing means for separating the incoming and outgoing beams. Maximizing the aperture area at the top of the tube is important in ensuring that an adequate signal reaches the detector, because the tube/IRE portion of the system has the system's lowest radiation throughput. At the IRE location, the radiation should be adequately separated on its incoming and outgoing paths; and it must have an appropriate angle of incidence on the sidewalls of the IRE.

BRIEF DESCRIPTION OF THE DRAWINGS

FIG. 1 is a vertical cross-section of a container showing the operating environment of the spectrometry system of the present invention;

FIG. 2 is a schematic showing an optical system which incorporates the present invention;

FIG. 4 is an enlarged view of a first possible interface between the lower end of the elongated tube and the IRE;

FIG. 5 is an enlarged view of a second possible interface between the lower end of the elongated tube and the IRE;

FIG. 6 is an optical ray diagram illustrating the effects of the focused radiation at the surface of an IRE mounted at the lower end of a tube;

FIG. 7 shows a possible structure for more securely positioning an IRE at the lower end of the elongated tube; and FIG. 8 shows a potential modification of the optical system shown in FIG. 2.

DETAILED DESCRIPTION OF SPECIFIC EMBODIMENTS

Figure 3A:
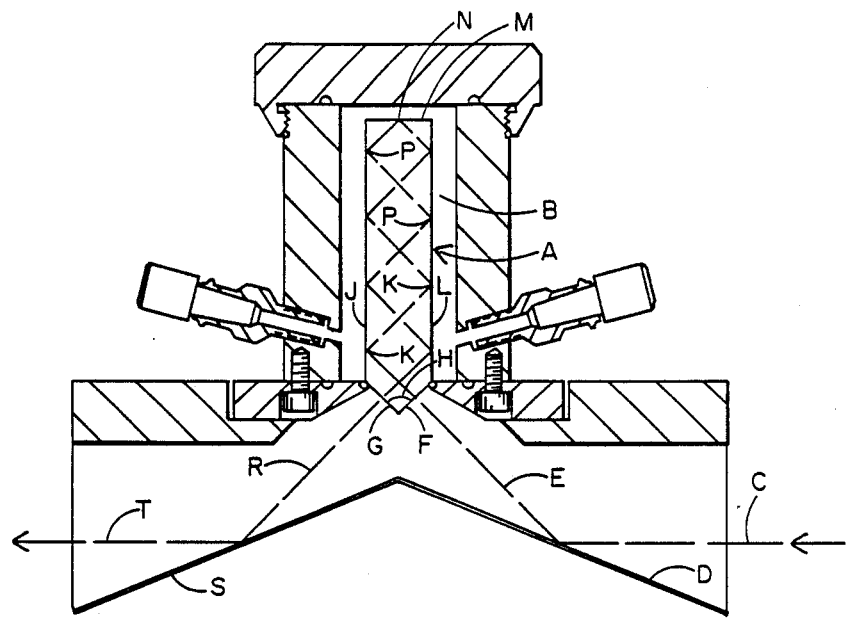
FIGS. 3A and 3B show a typical IRE supplied by the Harrick Corporation, FIG. 3A in cross-section, and FIG. 3B as an isometric illustrating the shape of the IRE "roof"

As stated above, the problems solved by the present invention relate to the need for spectrometric analysis of material in containers, usually large containers (drums, kettles, etc.). Such containers have various uses.

One of the most important uses is that of "batch process kettles", wherein liquid in a container is processed. Such processing usually involves chemical reactions, but it might also involve the non-reactive mixing of ingredients. In such processing kettles, the availability of "in-situ", real-time spectroscopic analysis during the processing period would be of great practical value. It would provide information as to the progress of the processing, thereby permitting timely determination that the process has been completed. It would also provide valuable insights leading to possible improvements in future processing procedures.

Another major use of the present invention relates to material in "storage drums". Because of the problem of material changes (deterioration) due to lengthy storage, it is desirable (and may be required by laws or regulations) to be able to promptly analyze the current condition of the material. Furthermore, in the case of hazardous or highly reactive materials, it is often desirable to positively identify a material (independent of its labeling) prior to using it in a process.

Efforts have been made to obtain spectroscopic analysis of liquids in batch kettles or storage drums by using "extractive sampling", i.e., pumping liquid out of the container, and subjecting it to analysis externally of the container. However, such efforts have often been abandoned because of the difficulties encountered in trying to subject the extracted material to the same temperature and pressure conditions as those existing inside the container.

The dimensional parameters of the problem are intimidating. The desired location of the internal reflection cell may be as much as 60 inches below the cover of the container; and the desired diameter of the elongated tube may be as small as 2 inches.

In FIG. 1, whose dimensions are not intended to represent the desired proportions, a large container 20 is shown, which is completely enclosed and sealed. An internal stirring paddle 22 is generally used, driven by an externally-located motor 24. The openings for supplying fluids to, and removing them from, the container are not shown in FIG. 1.

A spectrometer-associated structure for analysis of the material inside the container comprises an elongated tube 26 extending into the container, and an internal reflection element (IRE) 28 supported by, and extending from, the lower end of tube 26. It is desirable to locate the IRE 28 as far down in the container 20 as possible, so that the analytical function can be performed even with a relatively small amount of material in the container.

Inside elongated tube 26 (which may be circular or rectangular in cross-section), infrared radiation is directed downwardly and into IRE 28, and is returned upwardly to exit from the top of the tube, after it has been altered by its reflected contacts with the internal sides of IRE 28. In FIG. 1, an optical device for reflecting radiation going into, and coming out of, the tube 26 is indicated at 30; and the associated spectrometry apparatus at 32.

FIG. 2 shows schematically the optical system which provides the desired analytical sampling. A collimated entering beam 34 (represented in the figure by interrupted lines) traveling from an interferometer (not shown) is reflected by a parabolic reflector 36, and travels as a converging beam 38 to focus at an image plane focal point 39 on a flat mirror surface 40. A diverging beam 42 is thus directed toward a concave aspheric reflector 44, which reflects the beam into elongated tube 26 toward the lower end of the tube.

The reflection of beam 38 as beam 42 is accomplished in the system of FIG. 2 by a "rooftop" reflector 46, which functions as a "mechanical beamsplitter", because it separates the beam traveling toward reflector 44 from the returning beam.

The diverging entering beam 42 is reflected by reflector 44 to provide a converging beam 48, whose object plane focal point is at 50 on one surface of the apex, or rooftop-shaped upper end, of IRE 28. After the radiation has been reflected inside IRE 28, it will return to a point 52 on the other surface of the apex, or rooftop-shaped upper end, of IRE 28. This returning beam will then travel as a diverging beam 54 (represented in the figure by dashed lines), which exits from the top of tube 26, and is reflected by concave aspheric reflector 44 toward the mechanical beamsplitter 46.

The returning beam, after reflection by mirror 44, is a converging beam 56 which focuses at an image plane focal point 57 on the mirror surface 58 of rooftop reflector 46. Because this returning radiation is coming from a point 52 at the top of IRE 28, which point is displaced from the point 50 at which it entered the IRE, the returning beam 56 is slightly displaced from the entering beam 42. It, therefore, is reflected in the opposite direction by rooftop reflector 46, and travels as a diverging beam 60 toward a mirror 62. The mirror 62 may be a parabolic reflector which directs a collimated beam 64 to short focal length parabolic mirror 66, which focuses the beam at a detector 68.

In the preferred physical arrangement of the optical system, the reflectors 36, 44, 46, 62 and 66 would be located at the same horizontal level (not vertically spaced, as in the figure).

The reflector 44 has a very long focal length, with the result that the beam 48 at its object plane focal point 50 has characteristics similar to those of a collimated beam.

The long focal length mirror 44 may be a parabolic reflector, although an ellipsoidal reflector would be ideal. An ellipsoidal reflector would have the characteristic of being able to take light that comes from one location and refocus it at another location. So, in the ideal situation, mirror 44 would be an ellipsoidal reflector, with one of its foci being at the rooftop mirror 46, and the other of its foci being at the upper end of the IRE 28. In fact, however, for the typical geometry under consideration, a parabolic reflector can be used; and the distortion or aberration due to the parabola will be very slight, when compared to the beam spread involved. Parabolic reflectors are much easier to acquire than ellipsoidal reflectors; and in general they are easier to adjust and work with.

If the parabolic reflector 44 were to be so positioned that it would collimate the entering radiation, then the rooftop mirror 46 would be positioned in the focal plane of the mirror 44. However, because it is desired to condense the radiation which strikes the top of IRE 28, the location of parabolic mirror 44 is farther back, so that the spot 39 on the rooftop mirror 46 forms an image at the point 50 on the top of the IRE.

It is important, as previously stated, to have the maximum available radiation in the tube/IRE portion of the analytical system. To accomplish this, the optical imaging element at the top of tube 26 should use substantially the total available area of the top of the tube for both the incoming and the outgoing radiation. This means that the mirror 44, or other optical imaging element performing the same function, should be: (a) located as close as practicable to the top of tube 26; and (b) designed to reflect incoming and outgoing beams which approximately fill the top of the tube.

The aspheric (parabolic or ellipsoidal) reflector 44 could be replaced by other optical imaging elements, e.g., a Cassegrain objective, or a refractive element. The requirements of using maximum radiation area at the top of the tube, and of using a beamsplitter to separate the incoming and outgoing radiation, would, of course, apply to whatever imaging element is positioned above the tube.

Figure 3B:
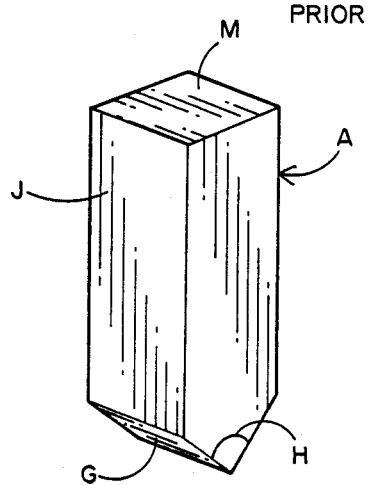

FIGS. 3A and 3B are included to provide a more readily understandable disclosure. They illustrate the structure of a standard, commercially available internal reflectance element (IRE), or attenuated total reflection (ATR) element. Element A is formed of transparent and externally polished material having the desired shape and index of refraction. Various materials may be selected to constitute the IRE, such as germanium, KRS-5, or zinc selenide.

The element A extends into an enclosed chamber B, into which liquid to be analyzed is introduced. In the structure of FIG. 3a entering and exiting ports are shown for controlling liquid flow. Radiation, which enters along path C (the dashed line represents the central ray of the beam), is reflected by a mirror D into element A along path E. The element A, as seen in FIG. 3B, has a rectangular cross-section. Its radiation entering (and exiting) end, which in FIGS. 3a and 3b is its lower end, is shaped like a rooftop (inverted), having two rectangular inclined surfaces F and G.

In the structure of FIGS. 3A and 3B, the included angle H between surfaces F and G is 90°; and the radiation E entering the element A is perpendicular to surface F. The radiation, therefore, continues on a straight line until it strikes the inner reflecting wall J of element A at K. The angle of incidence of the radiation on wall J is 45°; and its complementary angle is also 45°. The angle of reflection, which equals the angle of incidence, is 45°; and the radiation will be internally reflected across the IRE to strike the opposite inner reflecting wall L of the IRE (which is parallel to wall J) at a second point K. The incident angle at the second point K is also 45°. The radiation will continue to travel back and forth across the IRE until it reaches its end wall M (upper end in FIG. 3A).

As shown, the entering reflection strikes the end wall at N, and begins its return path, first striking inner reflecting wall J at P, and then being internally reflected across the IRE to strike the opposite inner reflecting wall L at a second point P. The returning radiation continues to be reflected, along a path parallel to that of the entering radiation, back and forth across the IRE until it exits along path R, which is perpendicular to exiting surface G. A mirror S reflects the radiation to direct it along path T. In an infrared spectrometer, the incoming radiation path C would bring radiation from an interferometer (or other input source); and the outgoing radiation path T would direct radiation toward an infrared detector.

The analytical function of the element A is accomplished by attenuation of the total internal reflectance which would occur in element A, if it were surrounded only by air. As long as the angle of incidence is above the "critical" angle, essentially total internal reflection will occur, unless the IRE is surrounded by material which causes an attenuation, or slight loss, of radiation at each of the reflection points K, P and N. The critical angle is that angle of incidence below which the radiation will exit through the wall of the IRE, and be "lost". If the angle of incidence is above the critical angle, it will be internally reflected, and will remain inside the IRE, except for the influence of attenuation.

In spite of "total" internal reflection above the critical angle of incidence, there is a small vector in the electromagnetic field that projects through the surface of the IRE. If there is a suitable material in contact with the outer surface of the IRE, the vector can "couple into" that material and be attenuated. That slight amount of attenuation is what is measured as the output signal. A significant benefit for mid-infrared measurements is that the effective path length of the vector is very short, only a few micrometers. Such attenuation is much easier to use than a very thin transmission cell, because the liquid around an IRE is free to move around, and only the first few microns of it affect the radiation inside the IRE. The amount of radiation absorbed can be adjusted by the length of the IRE, and by the amount of its surface area in contact with the liquid.

If the IRE is surrounded by air, the internal radiation will be totally reflected (if the angle of incidence is greater than the critical angle), because of the difference between the index of refraction of the air and the index of refraction of the IRE material. In the presence of a liquid, or other material, contacting the outside of the crystal, total reflection will no longer occur, because the indices of refraction of the contacting material and the IRE are much closer. Chemicals of interest in the field of infrared spectrometry have indices of refraction within the range of 1.3 to 1.8, and predominantly in the range of 1.5 to 1.7. The material used as the IRE should have an index of refraction somewhat higher than that of the liquid being analyzed, in order to obtain adequate attenuation (or absorption). Zinc selenide, as an example, has an index of refraction of 2.42.

Applicant is the first to suggest that it is feasible to obtain sample analysis in situ from a location deeply immersed in a container. The potential practical importance of the present invention is very significant, for the reasons discussed above. But, to applicant's knowledge, there has been no realization that the problem, or need, could be addressed in the manner disclosed in this application.

The primary considerations in providing a practical device are: (a) having the appropriate interface between the elongated tube 26 and the IRE 28; (b) having the appropriate optical elements in the system, so that the radiation entering and leaving the tube will follow separate paths; and (c) having sufficient radiation throughput to supply an adequate signal at the detector.

FIG. 4 illustrates one approach to the tube/IRE interface problem. If a tube 70 is used having adequate cross-sectional area, a pair of flat mirrors 72 and 74 can be mounted inside the tube, and so located that mirror 72 will reflect incoming radiation into an IRE 76, and mirror 74 will reflect radiation returning from IRE 76 back toward the top of the tube. If such a construction is used, the IRE rooftop 78 may be shaped similarly to the lower end of the IRE in FIGS. 3a and 3b, with an included rooftop angle of 90°.

The structure of FIG. 4 has the advantages that it permits use of a standard IRE shape, and provides a relatively wide separation of the entering and returning beams, as shown. It also would permit varying the internal reflection angle of the radiation (in the IRE) by adjusting the inclination of the flat mirrors 72 and 74. As shown in FIG. 4, the entering and exiting beams are perpendicular to the IRE upper surface through which they pass. As discussed in detail in explaining subsequent embodiments of the invention, the internal radiation can be redirected by causing radiation entering the rooftop to have an angle of incidence other than zero.

One disadvantage of the FIG. 4 embodiment is that it requires a larger tube cross-sectional area. However, the tube dimensions can still be maintained below the 2" diameter mentioned above. And, in any event, the radiation area at the top of the tube must be sufficiently large to obtain adequate signal strength, as explained above.

FIG. 5 shows a different arrangement. Extending into an opening in the lower end of a tube 80 is an IRE 82 having an apex angle at its upper end which causes the radiation to change direction as it enters and leaves the IRE. As shown, the IRE has a much "sharper" upwardly projecting roof 84, i.e., the included, or apex, angle between the inclined sides 86 and 88 of the roof is much less than 90°.

In determining the apex angle, identified as "a" in the figure, it is necessary to begin with the desired internal angle of incidence "b" at the IRE walls. Generally, the preferred angle of incidence "b" is 45°, as in the IRE of FIGS. 3a and 3b. A 45° angle is larger than the critical angle of incidence, but not so much larger that the attenuation is insufficient to provide a well-defined spectrum. In other words at that angle, and with the usual indices of refraction of the prism and sample material, the depth of the radiation absorption bands will be sufficient for effective spectrometric analysis.

Because of the long focal length of the radiation beam entering tube 80, it is assumed that its path 90 is essentially parallel to the reflecting sides 92 and 94 of IRE 82. After entering IRE 82, the radiation will follow a path 91, which is deflected from path 90 as a function of the angle of incidence and of the relative indices of refraction of air (1.0) and of the IRE material. This deflection is determined by Snell's Law, which states that the sine of the angle of incidence multiplied by the index of refraction of the first material (the air) equals the sine of the angle of refraction multiplied by the index of refraction of the second material (the IRE).

It is necessary to determine the value of angle "c", which is approximately one-half of angle a, since a vertical line (parallel to path 90) intersecting the upper edge of IRE 82 would bisect angle a. Assume that a line 96 is drawn which is perpendicular to inclined surface 88 and which intersects surface 88 at the entering point "X" of radiation path 90 into the IRE; and further assume that a line 98 is drawn which is perpendicular to IRE side 92 and which intersects side 92 at the reflection point "Y" of radiation path 91. Angle "d" is the angle of incidence of radiation path 90 on inclined IRE surface 88; and angle b is the angle of incidence of the radiation path 91 on side 92. The value of angle b has been chosen as 45°; and the value of its complementary angle "e" is also 45°.

By extending lines 96 and 98 to their intersection point "Z", a triangle XYZ is formed. Angle "f" (between sides ZX and ZY) is equal to angle c, because their respective sides are perpendicular to one another (96 is perpendicular to 88; and 90 is perpendicular to 98). The value of angle f (and thus of angle c) can be determined by dealing with the values of angles within triangle XYZ. The total value of its internal angles is 180°; and the value of the angle between sides YX and YZ is 135° (90°+45°). So the total value of angle f plus angle "g" (between sides XZ and XY) is 45° (180°−135°).

Angle g is the angle of refraction. Using Snell's Law, and assuming trial values of angle c, it is possible to determine at what value of angle c (which is assumed equal to angle f) the total of angles f and g will be 45°. With a zinc selenide IRE, having an index of refraction of 2.42, this condition is essentially reached when a value of 22.57° is assumed for angle c (and angle f). This provides a value of 67.43° for the angle of incidence (d), and a value of 22.431° for the angle of refraction (g). Adding the angles f and g produces almost exactly 45°.

If the IRE material used were germanium, another attractive material, which has an index of refraction of 4.0, the desired angle relationships would be attained with a value of angle c (and of angle f) of 32.88°. The value of the angle of incidence (d) would be 57.12°; and the value of the angle of refraction (g) would be 12.12°. Adding f (32.88°) and g (12.12°) gives exactly 45°, as desired.

The value of angle a is twice that of angle c. So, if a zinc selenide IRE is used, the desired apex angle would be approximately 2×22.57=45.14°. If a germanium IRE is used, the desired apex angle would be approximately 2×32.88=65.76°.

FIG. 6 illustrates the manner in which the entering and returning radiation relates to the upper end of the IRE element. A triangular IRE element 100 is shown, in order to simplify the illustration. The only internal reflection surface of the IRE 100 is its bottom surface 102. As shown by the downwardly pointed arrows, radiation coming from the top of the tube (not shown) passes through one inclined top surface 104 of IRE 100. After being internally reflected at surface 102, radiation returning to the top of the tube passes through the other inclined top surface 106 of IRE 100, as shown by the upwardly pointed arrows.

Both the incoming and exiting radiation paths "flood" the available upper surfaces 104 and 106 of the IRE element. Although the term "focal point" has been used above, the inherent radiation spread will easily fill the upper surfaces of the IRE, whose cross-sectional area is in the neighborhood of one square centimeter. The image area of the radiation at the object plane (the top of the IRE) is two to three square centimeters.

The shaded column 108 represents the shaded area at the tip of the IRE, which is not available for IRE modified radiation. The entering ray 110, which forms the right vertical edge of shaded area 108, returns from the IRE as the ray from the left corner of the IRE roof. And the entering ray 112, which is directed toward the right corner of the IRE roof, returns from the IRE along the left vertical edge of shaded area 108.

As shown in FIG. 7, the existence of shaded area 108 may conveniently be used as the location of a mechanical retaining member 114, which engages the center of the roof of an IRE 116. The lower end of IRE 116 is supported by a horizontal wall 118, which is formed as an integral part of elongated tube 120. The combination of retaining member 114 and wall 118 provides a positive positioning structure for the IRE. Windows 122 and 124 in the tube sidewalls permit contact of the surrounding material with the IRE 116.

FIG. 8 shows another embodiment of the invention, in which the elongated tube functions as an internally reflecting light pipe. The FIG. 8 embodiment, in effect, sacrifices separation of the entering and exiting radiation beams, in order to simplify the radiation transfer from the top of the tube to the IRE.

In the FIG. 8 version, an optical imaging element 130, such as a parabolic or ellipsoidal mirror, is located a suitable distance above the top of a tube 132, and reflects a converging radiation beam 134 toward a focus at its object plane 136. The subsequently diverging beam 138 is reflected back and forth inside tube 132, whose internal surface is coated with a highly reflecting material, such as gold. An IRE 140 is supported at the bottom of tube 132. The tube 132 and IRE 140, which preferably have the same cross-sectional shape and substantially the same cross-sectional area, may be either circular or square in cross-section. The cross-sectional tube area, instead of being chosen to accommodate maximum infrared radiation beam area, is chosen to be approximately equal to the cross-sectional IRE area.

The tube 132 functions essentially as a light pipe. Radiation focused at its upper end is reflected back and forth down through the tube. In order to avoid excessive radiation losses resulting from multiple tube reflections, the angle of incidence of radiation on the tube walls should be large enough that the total number of tube wall reflections during the round trip is no more than 10–20. The range of angles of the radiation striking the IRE will be approximately the same as the range of angles of the beam focused at the upper end of the tube.

In effect, in FIG. 8, the focus of mirror 130 is displaced from one end of the tube to the other. The purpose is to obtain results similar to those which would be obtained if it were feasible to locate the IRE at the initial focus 136.

This embodiment has certain advantages. It requires a minimum cross-sectional area, so that it allows the probe to be quite narrow. Also, if the probe is deflected due, for example, to pressure from moving liquids inside the container, as might be the case in a reactor, the radiation still will be piped down through the tube even as the tube tends to bend one way or the other. It would, therefore, be unnecessary to maintain an image at the top of the IRE strictly through proper alignment of the optics. However, with the system of FIG. 8, it is not possible to keep the incident radiation focused on one side of the IRE roof, and the outgoing radiation emergent through the other side of the IRE roof. Essentially, the radiation is jumbled on both sides. As a result, the radiation leaving the IRE will also be more or less uniformly distributed between the two sides. Due to this mixing, it is not possible to separate the incoming and outgoing beams by means of spatial division in an image plane, as was done in FIG. 2. Instead, the two beams will always overlap and can only be separated with some sacrifice of signal.

In FIG. 8, a different beamsplitter arrangment is used for the incoming radiation from that used in FIG. 2. Although a rooftop, or half-image splitting, reflector could be used, a more generalized beamsplitter is shown, i.e., a 50% transparent beamsplitter 142. The incoming beam 144 from the source is partially reflected and partially transmitted by beamsplitter 142. And the beam returning from reflector 130 is partially transmitted and partially reflected by beam-splitter 142, the reflected beam 146 being focused by a reflector 148 at a detector 150.

Figure 9:
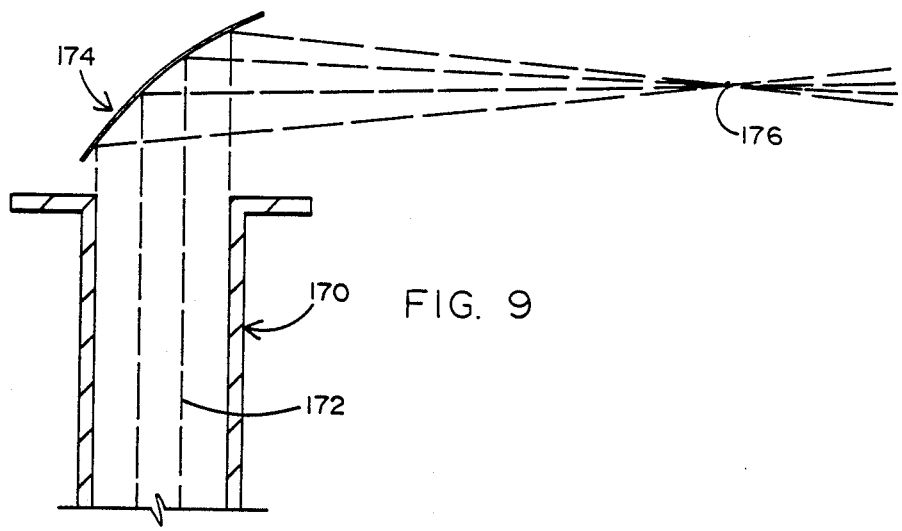
Figure 10:
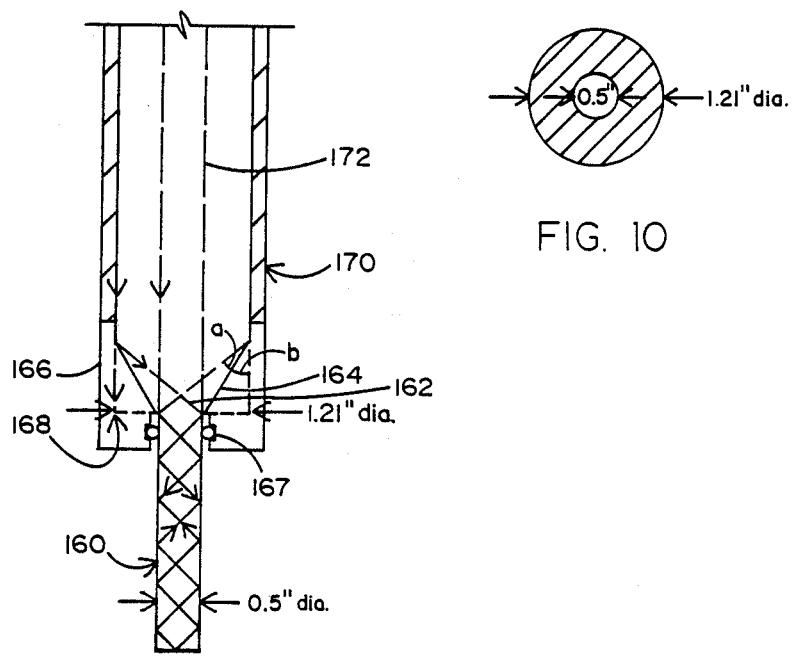

FIGS. 9 and 10 illustrate a further embodiment, having some specific advantages over those already discussed, and therefore, currently the preferred embodiment. This embodiment utilizes the approach illustrated in FIG. 4, with the exception that the IRE element is now assumed to have a circular cross-section. This simplifies the task of providing a seal between the optical path and the liquid being analyzed, by allowing the use of one or more annular "O" ring seals 169.

In FIG. 9, a circular cross-section IRE element 160 is shown, which has a conical (convex) upper end 162 having a 90 degree apex angle. Coupling of the radiation into the IRE is accomplished by means of a conical (concave) reflecting surface (i.e., circular cross-section), which may be machined in a block of metal 166. With a 45 degree IRE apex angle, the surface of the reflecting cone 164 will make an angle of 22.5 degrees with the vertical axis (i.e.: angle a=angle b=45°/2). The combination of the conical IRE point and the conical reflector has a unique and very useful optical property, in that the reflected image of the IRE surface will consist of an annulus lying in the plane 168 (as indicated by the dotted marginal rays and the dotted image).

If the IRE diameter is 0.5", the annular image will have inner and outer diameters of 0.5" and 1.21", respectively, (see FIG. 10). The area of this annular image (shaded) is much larger than the actual area of the IRE's upper surface, thus increasing the effective receiving area for IR radiation. For the example chosen, the unusable 0.5" diameter inner circle (of reflector 164) corresponds to only 17% of the total area being illuminated.

Note that, for uniform illumination, the radiation striking the IRE will tend to be concentrated near the tip (i.e., the portion corresponding to the outer area of the annular image). Since the area near the periphery of the IRE will receive a lower concentration of radiation, this area can be used to provide a bearing surface for mounting of the IRE, without sacrificing a significant amount of signal.

In this embodiment, the IRE and conical reflector are supported at the end of a cylindrical hollow reflecting tube 170 with an inner diameter equal to the maximum diameter of the reflector cone 164. This diameter, in turn, is determined by the position of the marginal rays which just strike the end 162 of the IRE 160. For convenience in machining the conical reflector 164 in block 166 (which also functions as a support for the IRE) this block may be a separate part from the cylindrical tube.

In view of the large effective target diameter, the optimum coupling of radiation to the IRE is accomplished by using a nominally collimated radiation beam 172. As shown in FIG. 9, an imaging element 174 above the tube is positioned so that its focal point is coincident with a point of focus 176 of the incoming radiation. If, in addition, the concepts of common assignee application Ser. No. 895,211 are incorporated in the optical design, an image of the interferometer aperture will form at the upper end of the tube 170. At this location, the beam diameter will typically be 1", with a divergence angle equal to that of the interferometer (typically 1°, depending on spectral resolution). Thus the radiation can be effectively coupled into the tube. With a divergence of 1°, a marginal ray will incur no more than one reflection in traveling the length of a 60" tube. Reflection losses will thus be minimal. At the same time, the well-collimated nature of the beam striking the IRE will lead to highly efficient IRE performance.

It should be noted that the design of FIGS. 9 and 10 achieves efficient performance while requiring an inner tube diameter of only about 1.21". This leaves space within the available 2" clearance for a heating element and an outer sleeve if desired (not shown). These may be necessary for some applications to prevent condensation of chemicals on the surfaces of the tube or the IRE.

FIGS. 11-13 illustrate a mechanism which may be used to mechanically insert the elongated tube into, and remove it from, a given container. This concept of simplified insertion and removal of the tube/IRE combination is an adaptation of the invention disclosed in a copending common assignee application (Attorney File No. LPC-13). The purpose of that application is to provide an articulated supporting structure which carries an internal reflectance element, and which permits the position of that element to be readily moved into and out of sample immersion.

Adapting the articulated supporting structure to the very long, small diameter tube of the present invention requires a more complex mechanism because the tube must be lifted and lowered in a vertical line (without tilting) through a distance of several feet. In order to accomplish this function, a scissors-like tubular linkage is suggested.

The lower end of long tube 180 carries IRE element 182; and its upper end is supported by a straight-line tube 184, inside which radiation travels in a purged environment. Tube 184 is secured to a corner tube 186, which is also secured to a straight-line tube 190. Inside corner tube 186 is a parabolic reflector which changes the direction of the radiation path, and also changes it from an incoming collimated beam to a focusing beam. The other end of tube 190 is connected to a corner tube 192, by means of a connection which includes a rotary member 196, i.e., a member which permits relative rotation between tube 190 and tube 194 during insertion of long tube 180 into, and its retraction from, a container.

A straight-line tube 198 is secured at one end to corner tube 192 and at the other end to a corner tube 200. Inside corner tube 192 is a parabolic reflector 194, and inside corner tube 200 is a parabolic reflector 202. The reflectors 194 and 202 are confocal paraboloids, whose confocal radiation path provides a throughput-conservation benefit in the long radiation path required to accommodate the insertion/retraction linkage.

Corner tube 200 is connected by a short straight-line tube 206 to a corner tube 208. Rotary movement in this connection is permitted by a rotary member 204. Inside corner tube 208 is a flat 45° reflector 210, which redirects the collimated radiation beam in tube 206 as a collimated beam in a straight-line tube 212. The other end of tube 212 is connected to a corner tube 214, inside which is another flat 45° reflector 216. Reflector 216 redirects the collimated beam through a short tube 220 to a beamsplitter 224 mounted inside a tube 222 having three ports. An incoming beam from an interferometer, as indicated by a first arrow, passes through one port; and an outgoing beam to a detector, as indicated by a second arrow, passes through another port.

A rotary member 218 permits relative movement between tube 220 and tube 214. As seen in the side view FIG. 13, the inclusion in the linkage of the three rotary members 196, 204 and 218 permits pivotal motion at both ends of tubes 198 and 212.

FIG. 11 shows the linkage position with the tube 180 and IRE 182 inserted in the container. FIG. 12 shows the linkage position with the tube 180 and IRE 182 fully retracted from the container. FIG. 13 shows the scissors effect by means of which the relative rotation of members 196, 204 and 218 allows the tube 180 to be inserted and retracted along a linear vertical path. This is necessary to move tube 180 up and down through the small access opening in the top of the container.

In addition to permitting the ready use of the tube-/IRE unit in a plurality of different containers, the linkage of FIGS. 11-13 permits ready access to the tube/IRE unit for the purpose of cleaning it between its insertion in different samples.

From the foregoing description, it will be apparent that the apparatus disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. An internal reflection spectroscopy system for in situ analysis of sample material confined in a container, comprising:
   a source of infrared analytical radiation which is directed toward the sample;
   a detector which receives sample-altered infrared radiation from the sample;
   an elongated hollow tube extending from the top of the container a substantial distance toward the bottom of the container, and into the sample material;
   an internal reflectance element mounted at the lower end of the tube which receives incoming radiation, reflects it internally, while permitting sample-caused attenuation, and returns the attenuated radiation on a path substantially parallel to that of the incoming radiation; and
   aspheric radiation reflecting means adjacent the top of the tube which receives source-provided entering radiation, directs such entering radiation downwardly through the tube and into the internal reflectance element, and directs sample-attenuated radiation returning upwardly through the tube toward the detector.

2. The internal reflection spectroscopy system of claim 1 in which:
   the upper end of the internal reflectance element has an acute apex angle formed by two flat converging surfaces.

3. The internal reflection spectroscopy system of claim 2 in which:
   the aspheric radiation reflecting means is a parabolic or ellipsoidal mirror which receives an image from a focal point and transforms that image to a focal point on one of the flat converging upper end surfaces of the internal reflectance element.

4. The internal reflection spectroscopy system of claim 3 in which:
   the index of refraction of the internal reflectance element and the angle of incidence of the incoming radiation on the surface of the upper end of that element are such that the radiation is reflected back and forth between the side walls of the element at an angle of incidence of approximately 45° with both walls.

5. The internal reflection spectroscopy system of claim 4 in which:
   the reflected radiation returning from the internal reflectance element to the mirror adjacent the top of the tube passes through the flat converging upper end surface of the internal reflectance element other than the upper end surface through which the entering radiation passed.

6. An internal reflection spectroscopy system for in situ analysis of sample material confined in a container, comprising:
   a source of infrared analytical radiation which is directed toward the sample;
   a detector which receives sample-altered infrared radiation from the sample;
   an elongated hollow tube extending from the top of the container a substantial distance toward the bottom of the container, and into the sample material;
   first radiation-directing means located at the lower end of the tube which receives incoming radiation from, and returns it to, the top of the tube;
   said first radiation-directing means comprising an internal reflectance element in which the radiation is both internally reflected and altered by the sample material; and
   second radiation-directing means above the tube which receives source-provided entering radiation, directs such entering radiation downwardly through the tube, receives radiation returning upwardly through the tube, and directs such returning radiation toward the detector.

7. The internal reflection spectroscopy system of claim 6 in which:
   the internal reflectance element of the first radiation-directing means has a top surface so shaped that its center projects upwardly and its outer portions slope downwardly from its center; and
   the second radiation-directing means directs the downward path of the entering radiation toward one sloping top surface of the internal reflectance element, and receives returning radiation on an upward path emanating from the other sloping top surface of the internal reflectance element.

8. The internal reflection spectroscopy system of claim 7 in which the first radiation-directing means also comprises:
   a first mirror surface located at the bottom of the tube which directs downwardly traveling radiation into one sloping top surface of the internal reflectance element; and
   a second mirror surface located at the bottom of the tube which directs upwardly radiation exiting through the other sloping top surface of the internal reflectance element.

9. The internal reflection spectroscopy system of claim 7 in which:
   the downward and upward radiation paths in the tube extend directly from the second radiation-directing means to the respective sloping top surfaces of the internal reflectance element; and
   the angles between such radiation paths and the respective sloping top surfaces of the internal reflectance element are such that the radiation inside such element is so diffracted as to travel at an angle of incidence which provides attenuated total reflectance for sample analysis.

10. The internal reflection spectroscopy system of claim 6 in which:
    the second radiation-directing means comprises an aspheric mirror which is located close to the top of the tube, and which has a first focus at an image plane in the source-provided radiation and a second focus at an object plane at the top of the internal reflectance element.

11. The internal reflection spectroscopy system of claim 6 in which:
    the elongated hollow tube is a light pipe having an internally reflecting surface which causes multiple reflections of radiation as it travels downwardly or upwardly in the tube; and
    the second radiation-directing means comprises an optical element which receives source-provided radiation and focuses such radiation at the top of the tube.

12. The internal reflection spectroscopy system of claim 6 in which:
    the internal reflectance element has a circular crosssection and a convex conical upper end; and
    the first radiation-directing means also comprises a concave conical reflecting surface which directs entering radiation into and receives exiting radiation from the upper end of the internal reflectance element.

13. The internal reflection spectroscopy system of claim 12 in which:
    the second radiation-directing means directs a substantially collimated beam downwardly through the tube toward the first radiation-directing means.

14. The internal reflection spectroscopy system of claim 6 which also comprises:
    movable tube-supporting means connecting to the top of the tube; and
    retracting means connected to the tube-supporting means for raising the tube out of the container without changing its vertical orientation.

* * * * *